United States Patent
Nagamura

(10) Patent No.: US 6,740,896 B2
(45) Date of Patent: May 25, 2004

(54) SENSITIVITY ADJUSTING METHOD FOR PATTERN INSPECTION APPARATUS

(75) Inventor: Yoshikazu Nagamura, Hyogo (JP)

(73) Assignee: Renesas Technology Corp., Tokyo (JP)

( * ) Notice: Subject to any disclaimer, the term of this patent is extended or adjusted under 35 U.S.C. 154(b) by 9 days.

(21) Appl. No.: 10/269,876

(22) Filed: Oct. 15, 2002

(65) Prior Publication Data

US 2003/0201410 A1 Oct. 30, 2003

(30) Foreign Application Priority Data

Apr. 24, 2002 (JP) ........................................ 2002-122312

(51) Int. Cl.[7] .............................................. G01N 21/88
(52) U.S. Cl. .............................. 250/559.45; 250/559.06
(58) Field of Search .................... 250/559.45, 559.46, 250/559.4, 559.06, 559.04, 578.1; 356/237.2, 237.3, 237.4

(56) References Cited

U.S. PATENT DOCUMENTS 5,105,092 A * 4/1992 Natsubori et al. ..... 250/559.06
6,498,333 B1 * 12/2002 Christensen ......... 250/214 AG

FOREIGN PATENT DOCUMENTS

| JP | 07-120404 | 5/1995 |
|----|-----------|--------|
| JP | 11-84630  | 3/1999 |

* cited by examiner

*Primary Examiner*—Thanh X. Luu
*Assistant Examiner*—Seung C Sohn
(74) *Attorney, Agent, or Firm*—McDermott, Will & Emery

(57) ABSTRACT

In a pattern inspection apparatus inspecting a pattern formed on a device and the like with a plurality of inspection lights, a sensitivity adjustment method in which respective optical systems associated with the inspection lights are efficiently and precisely checked to adjust the sensitivity thereof is attained. The sensitivity adjusting method for adjusting sensitivity of the pattern inspection apparatus performing inspection with a plurality of inspection lights includes the steps of preparing a sensitivity adjusting substrate divided into a plurality of regions to which identical reference patterns are provided, and scanning the reference patterns with the plurality of inspection lights making one of the plurality of inspection lights respectively correspond to one of the reference patterns, after attaching the sensitivity adjusting substrate to the pattern inspection apparatus.

10 Claims, 7 Drawing Sheets

SENSITIVITY ADJUSTING METHOD FOR PATTERN INSPECTION APPARATUS

BACKGROUND OF THE INVENTION

1. Field of the Invention

The present invention relates to a method for adjusting sensitivity of a pattern inspection apparatus which detects defects or foreign objects in a pattern of a photomask substrate or a semiconductor substrate utilized for manufacturing a semiconductor device.

2. Description of the Background Art

In a pattern inspection apparatus for detecting defective part in a pattern of a semiconductor wafer, a liquid crystal panel, a photomask or the like, a plurality of inspection lights 101, 102 and 103 are used to reduce the inspection time, as shown in FIG. 11. A method has been employed in which these plurality of lights are directed to a plurality of different portions on an inspected surface 122 of a substrate 150 of aforementioned device, the photomask or the like, to proceed with the inspection concurrently. In this inspection method, optical system elements such as an objective lens, an imaging element and the like are provided for each of the plurality of inspection lights 101, 102 and 103 which are output from the inspection apparatus. As such, each optical system needs to be adjusted to provide identical detection sensitivity for every light.

When adjusting each optical system, conventionally, only one of the inspection lights is driven to test its sensitivity, while the rest of inspection lights are shielded. Specifically, one inspection light scans pattern region 122 of a sensitivity adjusting substrate 110 to check its detection sensitivity. Next, only one of the rest of inspection lights is driven in a similar manner to check its detection sensitivity, and then these results are compared to be adjusted to the same level.

According to the above method for checking the sensitivity, the sensitivity check must be performed for each inspection light and thus requires considerable time for checking and adjusting sensitivity. Additionally, when a plurality of lights are provided, not every inspection light may be able to scan the identical portion of the inspected surface. In such a case, the inspected substrate may require to be, for example, rotated to change its direction. This rotation, however, changes the direction of the pattern of the inspected region, i.e., the direction of the defects or foreign objects to be detected. This rotation fluctuates a reflecting light or a scattering light for detection, hence hinders checking the correct limitation of detection sensitivity and to adjust the detection sensitivity for each inspection light.

Conventionally, as a sensitivity correction mask for a foreign objects inspection apparatus, a mask for improving identification of foreign objects has been disclosed (for example, Japanese Patent Laying-Open Nos. 11-84630 and 7-120404). On the other hand, a technique for efficiently adjusting sensitivity of optical systems associated with a plurality of inspection lights has never been disclosed.

SUMMARY OF THE INVENTION

The object of the present invention is to provide a sensitivity adjusting method for a pattern inspection apparatus, which performs inspection of patterns formed on a device or a photomask with a plurality of inspection lights, for efficiently and precisely checking and adjusting each of the optical systems associated with the inspection lights.

The sensitivity adjusting method for the pattern inspection apparatus according to the present invention is for adjusting the sensitivity of the pattern inspection apparatus inspecting patterns on a device formed during manufacture thereof, with a plurality of inspection lights. The present method includes the steps of preparing sensitivity adjusting substrate divided into a plurality of regions to which identical reference patterns are respectively provided, and scanning reference patterns with the plurality of inspection lights making one of said plurality of inspection lights respectively correspond to one of said reference patterns, after attaching to the sensitivity adjusting substrate to the pattern inspection apparatus.

With this configuration, a plurality of inspection lights can scan the identical reference patterns in respective region to obtain sensitivity information of respective optical systems associated with the inspection lights. As a result, efficiency is improved when checking the inspection sensitivity for a photomask or the like and adjusting the sensitivity. The aforementioned patterns on a device formed during manufacture thereof refers to the patterns formed on a various types of devices formed on a semiconductor substrate, specifically various types of semiconductor devices or liquid crystal panels or the like, and photomask patterns for forming such devices.

Further, base patterns may be formed by a semi-transparent film and programmed defects (i.e., defects deliberately formed for checking sensitivity) may be formed by transparent portions, such as gaps left by removing the semi-transparent film. Since the programmed defects are provided as such gaps, sensitivity of detecting foreign objects can be checked quantitatively.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

In the following, embodiments of the present invention will be described with reference to the drawings.

(First Embodiment)

Figure 1:
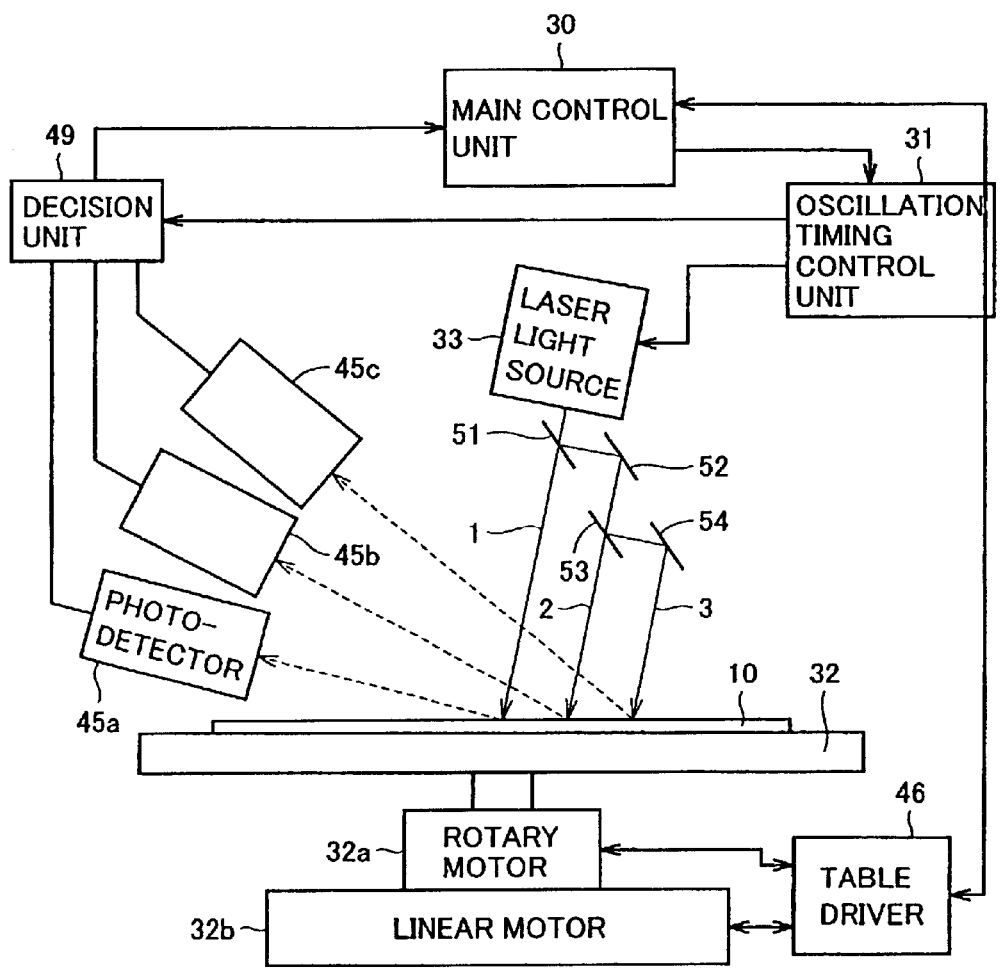
FIG. 1 schematically shows a configuration of a pattern inspection apparatus to which a sensitivity adjusting method according to a first embodiment of the present invention is applied.

In FIG. 1, a laser light, timed by the oscillation timing control unit 31 and oscillated from a laser light source 33, is divided into an inspection light 1 and a reflected light by the partially transmitting mirror 51. The reflected light changes its course at a totally reflecting mirror 52 and directed to the partially transmitting mirror 53 to be divided into a transmitted light, i.e., an inspection light 2, and a reflected light which is in turn reflected at the totally reflecting mirror 54 to be an inspection light 3. All of these inspection lights 1, 2 and 3 are directed to a sensitivity adjusting substrate 10. Sensitivity adjusting substrate 10 is mounted on a table 32 which is driven by a rotary motor 32a and a linear motor 32b. The rotary motor and the linear motor are controlled by a table driver 46.

The inspection lights 1, 2 and 3 directed to a prescribed region on the sensitivity adjusting substrate are respectively detected by separate photodetectors 45a, 45b and 45c. Each light received by the photo detector is input to a multichannel decision unit 49, where its sensitivity is checked and adjusted. Multichannel decision unit 49, oscillation timing control unit 31 and table driver 46 and the like are controlled by a main control unit 30 configured with a microcomputer.

Figure 2:
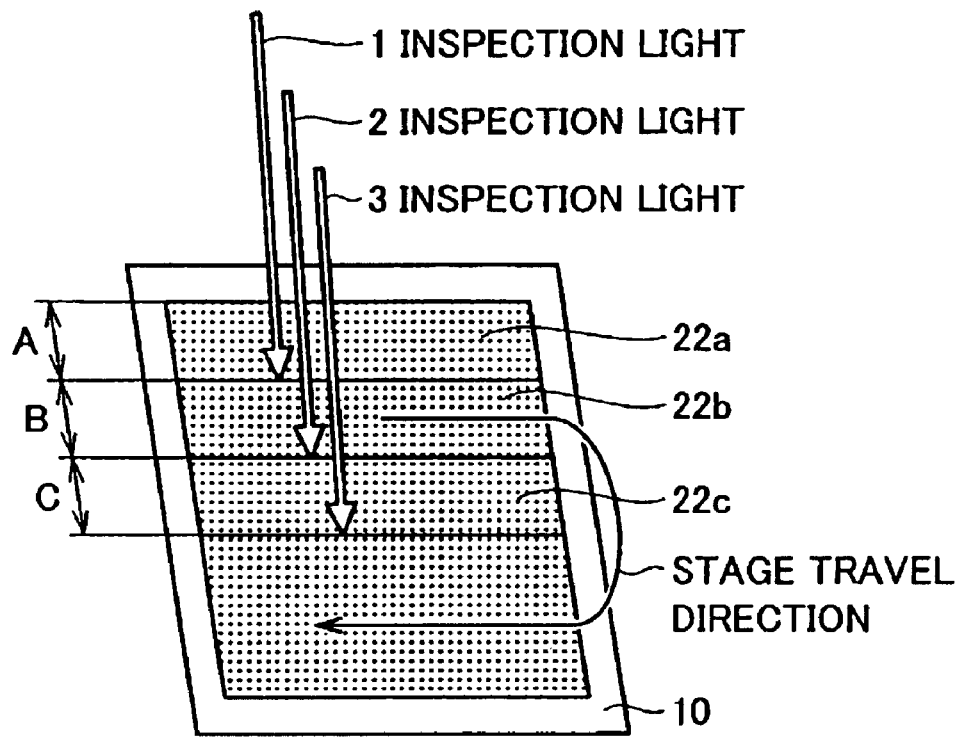
FIG. 2 is a perspective view related to a sensitivity adjusting method according to the first embodiment of the present invention.
Figure 3:
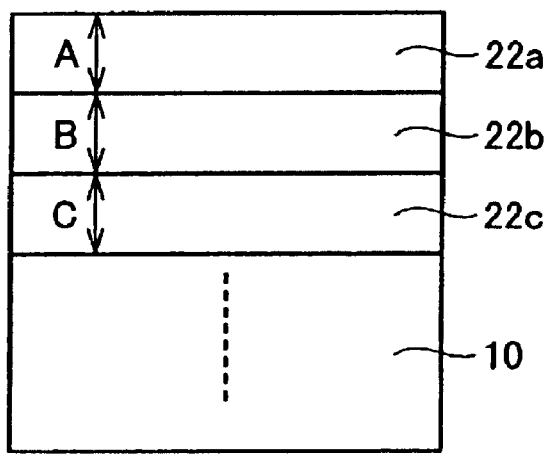
FIG. 3 shows a sensitivity adjusting substrate used in the method described in conjunction with FIG. 2.

FIG. 2 is a perspective view related to a sensitivity adjusting method according to a first embodiment of the present invention. FIG. 3 shows a photomask which is a sensitivity adjusting substrate employed in the sensitivity adjusting method. The object to be inspected is a photomask pattern formed on the photomask. Photomask 10 is divided into a plurality of regions A, B and C in which reference patterns 22a, 22b and 22c are respectively formed. These reference patterns include defects formed by, for example, arranging a light shielding film deliberately.

In the above sensitivity adjusting method, the reference pattern may include a base pattern configured with a combination of line pattern and space pattern, and programmed defects which is a defective portion having at least one of light transmittance, refractive index or thickness different from the base pattern.

The light transmitting through or reflected on the programmed defects may be different, in intensity, phase or the like, from the light transmitting through or reflected on the base pattern as detected by the photodetector unit as a light receiving portion. Therefore, the programmed defects may be different from the base pattern in at least one of light transmittance, refractive index, or thickness. For example, the transmittance of the base pattern may be smaller than that of the programmed defects.

In the above sensitivity adjusting method, the reference pattern may include a simulation pattern region in which programmed defects are arranged in the base pattern, and defect-free pattern region configured of the base pattern.

With such a configuration, by comparing a light signal from the simulation pattern region and that from the defect-free pattern region, detection sensitivity can be checked and adjusted for respective optical systems associated with the inspection lights. Thus, efficient sensitivity adjustment may be attained.

Referring to FIGS. 2 and 3, sensitivity adjustment is performed using the photomask (sensitivity adjusting substrate) having identical reference patterns arranged respectively for a plurality of scan regions, which are to be scanned by the plurality of inspection lights. A plurality of inspection lights 1, 2 and 3 respectively scans the regions A, B and C. The stage, on which the sensitivity adjusting substrate is fixed, travels as indicated by an arrow in FIG. 2, so that the inspection lights scan the substrate from one edge to another, and then pass over the scanned regions to proceed. This travel is repeated several times depending on the size of the sensitivity adjusting substrate or the scanned area, or the size of captured image contributing to the sensitivity adjusting setting of the pattern inspection apparatus. The reference patterns for adjusting sensitivity are arranged adapted to the dimension of the region through which the inspection lights scan.

Figure 4:
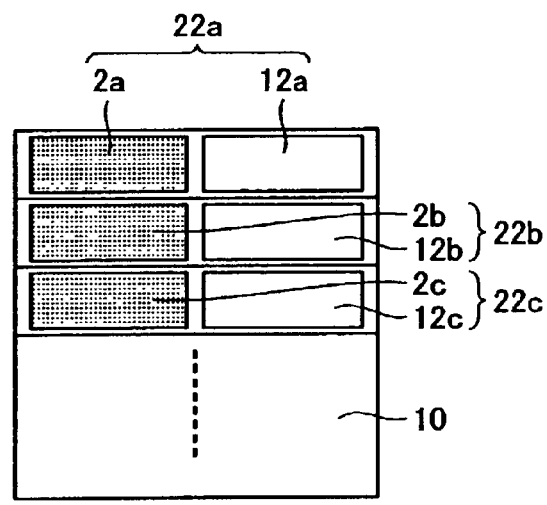
FIG. 4 shows a reference pattern formed on the sensitivity adjusting substrate in FIG. 3.

Images of the reference patterns are respectively obtained by each of the inspection lights 1, 2 and 3. These images are the same since they are derived from identical patterns for each of the regions A, B and C. The reference patterns include simulation patterns 2a, 2b and 2c in which programmed defects, i.e., defective portions deliberately formed with light shielding films, are arranged in a simple base pattern of a line/space pattern. The reference patterns further include defect-free patterns configured solely with aforementioned base patterns 12a, 12b and 12c. Therefore, the reference patterns are configured with simulation pattern regions 2a, 2b and 2c, and defect-free regions 12a, 12b and 12c as shown in FIG. 4.

By comparing lights from the simulation pattern regions 2a, 2b and 2c including programmed defects and those from the defect-free pattern regions 12a, 12b and 12c including defect-frees base patterns only, defect detection sensitivity can be valued and adjusted. In the simulation pattern regions including the programmed defects, the programmed defects can be regularly arranged, such as in order of size, to determine the detection limitation of the pattern inspection apparatus with respect to defect size, and hence, to determine its detection sensitivity. This detection sensitivity is determined by the defects provided to have regularly increased sizes for every inspection light, and thus the detection sensitivity of respective optical systems associated with the inspection lights can be adjusted uniformly when there is a variation in sensitivity among the inspection lights.

Figure 5:
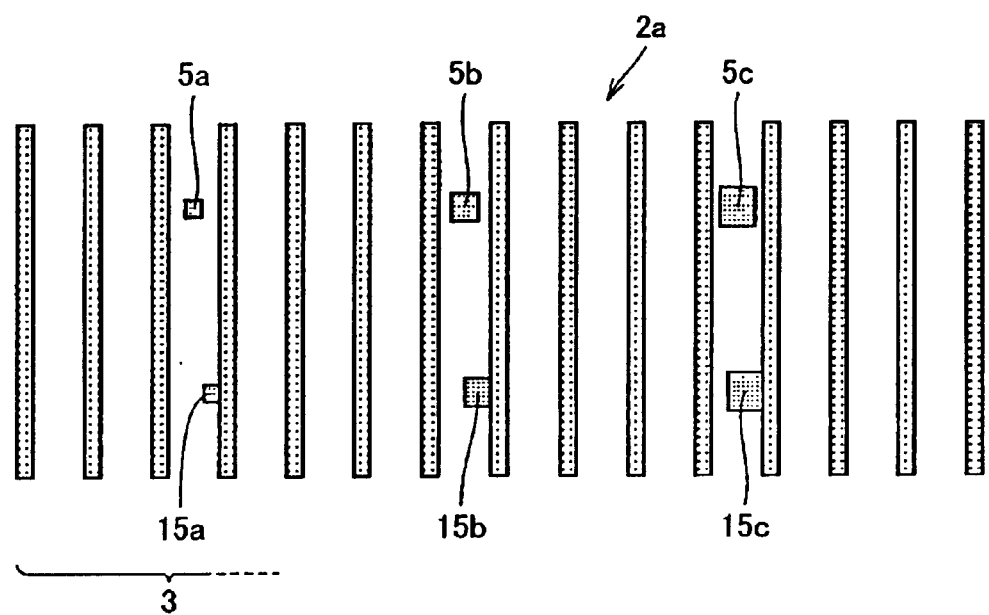
FIG. 5 shows a base pattern region including programmed defects in the reference pattern in FIG. 4.

FIG. 5 shows an example of the simulation pattern including the programmed defects. In this figure, a line/space pattern is employed as the base pattern, and light shielding film positive defects 5a, 5b and 5c being isolated, and protrusion defects 15a, 15b and 15c on the edge of light shielding film, are arranged as programmed defects. Since the base pattern and the programmed defects on the photomask are formed according to designing data, reference patterns can be formed almost identical. Specifically, with the most advanced photomask manufacturing technique, the variation in dimension can be suppressed to ±20 nm. This variation in dimension of the reference patterns on the photomask does not hinder the aforementioned uniform sensitivity adjustment of the optical systems associated with the inspection lights, since the defects detection sensitivity is at most about 100 nm.

By employing the sensitivity adjusting substrate having aforementioned identical reference patterns arranged in each of the regions, detection sensitivity of the optical systems and the like associated with a plurality of inspection lights can simultaneously be checked. As a result, the sensitivity adjustment of the pattern inspection apparatus can be performed efficiently, and thus the sensitivity adjusting time can be reduced.

(Second Embodiment)

Figure 6:
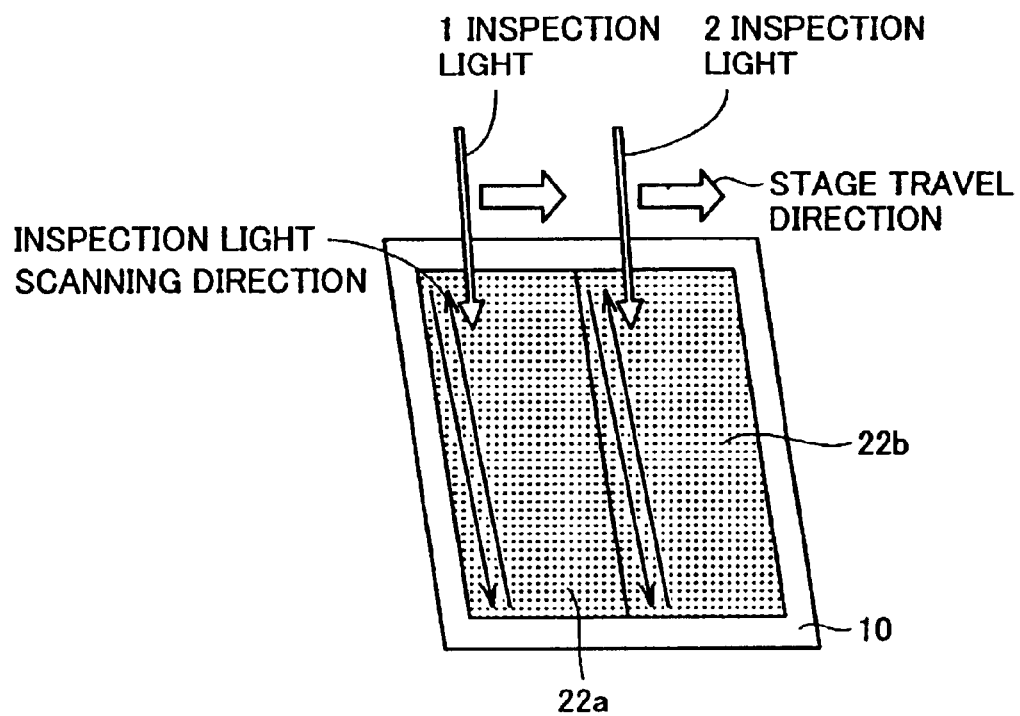
FIG. 6 is a perspective view related to a sensitivity adjusting method according to a second embodiment of the present invention.
Figure 7:
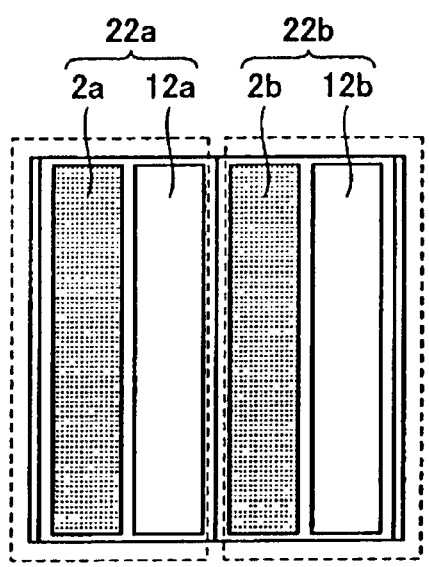
FIG. 7 shows a sensitivity adjusting substrate used in the method described in conjunction with FIG. 6.

In the present embodiment, two inspection lights are utilized as shown in FIG. 6 to scan two reference patterns formed on the photomask as the sensitivity adjusting substrate. As shown in FIG. 7, the reference patterns are configured with simulation pattern regions 2a and 2b including programmed defects, and defect-free pattern region 12a and 12b formed by base pattern only without any programmed defects.

Since the scanning arrangement and the covering region of the inspection lights differ depending on the pattern inspection apparatus, the sensitivity adjusting substrate may be employed in which reference patterns are arranged so as to conform with each pattern inspection apparatus. Each of the inspection lights can scan respective region concurrently. Accordingly, the sensitivity adjustment of respective optical systems associated with the inspection lights can be performed uniformly and efficiently, even different regions are separately scanned by the respective inspection lights.

(Third Embodiment)

Figure 8:
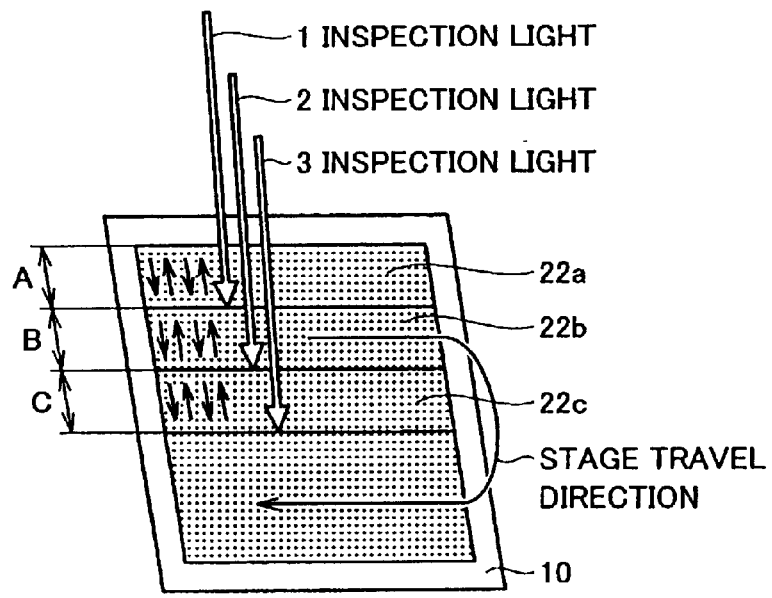
FIG. 8 is a perspective view related to a sensitivity adjusting method according to a third embodiment of the present invention.

As shown in FIG. 8, the present embodiment is characterized in that a scanning using a deflection element is superimposed to the scanning performed by the inspection lights, additionally to the travel of the stage. Specifically, a laser light is employed as a source of the inspection light, and the deflection element is used to drive the inspection light for scanning additionally to the travel of the stage. When the scanning width of each inspection light, i.e., the width of the region A in FIG. 8 is, for example, about 150 $\mu$m, the width of the reference pattern is to be 150 $\mu$m. The direction of the table travel is perpendicular to the width A.

By such stage travel direction and the deflection element scanning direction, reference patterns 22a, 22b and 22c can be scanned by moving each inspection light 1, 2 and 3 along longitudinal direction only once. These three reference patterns are identical, and thus inspection lights 1, 2 and 3 not necessarily perform scanning independently to check and adjust their sensitivity. Accordingly, sensitivity checking and adjustment are carried out efficiently.

(Fourth Embodiment)

A sensitivity adjusting method of the pattern inspection apparatus according to a fourth embodiment of the present invention is characterized in that a mercury lamp is employed as a source of the plurality of inspection lights. One mercury lamp may be provided for each inspection light, or a light from single mercury lamp may be split and directed to respective optical systems associated with inspection lights. When the mercury lamp is used, scanning by the inspection lights is preferably performed by the stage travel only.

By employing the mercury lamp as a source of the inspection lights, variety of the inspection light source is provided, while efficient sensitivity adjustment of the inspection lights is attained.

(Fifth Embodiment)

A sensitivity adjusting method of the pattern inspection apparatus according to a fifth embodiment of the present invention is characterized in that an image of the reference patterns is recognized by an imaging element. Specifically in the present embodiment, the inspection lights are directed to the reference pattern, and the lights reflected upon or transmitted through the reference pattern is introduced into the imaging element. The images of the reference patterns are recognized in the imaging element and corresponding patterns are compared with each other to detect defects and the like. Thus, the sensitivity of each inspection light is checked and adjusted.

By employing the imaging element as above, quantification of detection limitation of defects or automation of operation can easily be performed.

(Sixth Embodiment)

A sensitivity adjusting method according to a sixth embodiment of the present invention is characterized in that the inspection lights are directed to the reference patterns, and scattering lights from the defects of the reference patterns are detected by a photomultiplier tube. The sensitivity for detecting defects can be improved by employing the photomultiplier tube, and also automation or quantification will be facilitated.

(Seventh Embodiment)

In a sensitivity adjusting substrate in the sensitivity adjusting method according to a seventh embodiment of the present invention, the reference pattern is employed in which programmed defects are arranged regularly in order of size. For example as shown in FIG. 5, the defect size is increased from left to right. With such a regular arrangement in the defect size, the detection limitation with respect to the size of the defects can be checked, hence the defect detection sensitivity can be checked quantitatively.

(Eighth Embodiment)

Figure 9:
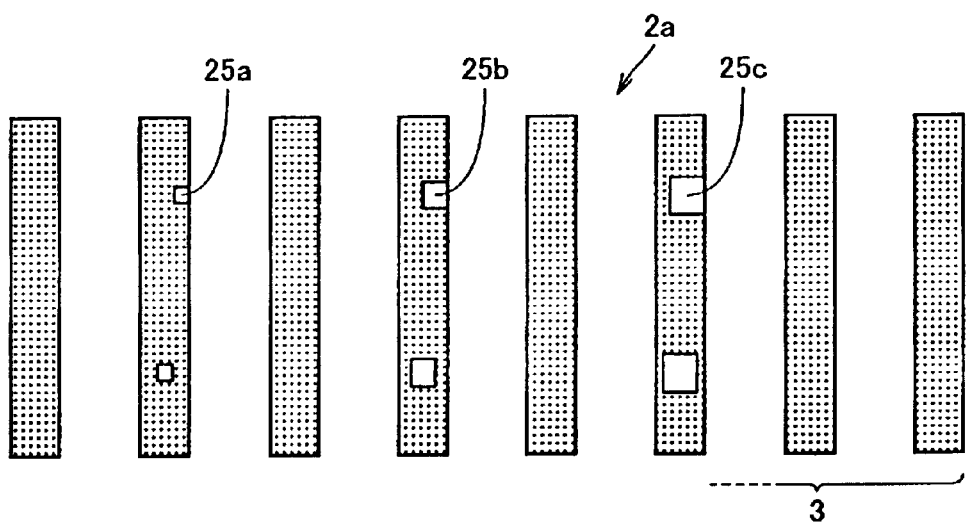
FIG. 9 shows a sensitivity adjusting substrate used in a method according to an eighth embodiment of the present invention.
Figure 10:
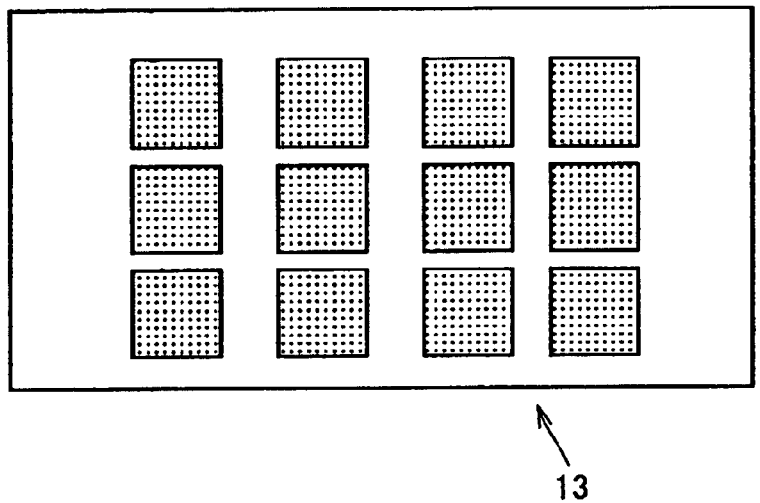
FIG. 10 shows another sensitivity adjusting substrate used in a method according to the eighth embodiment of the present invention.
Figure 11:
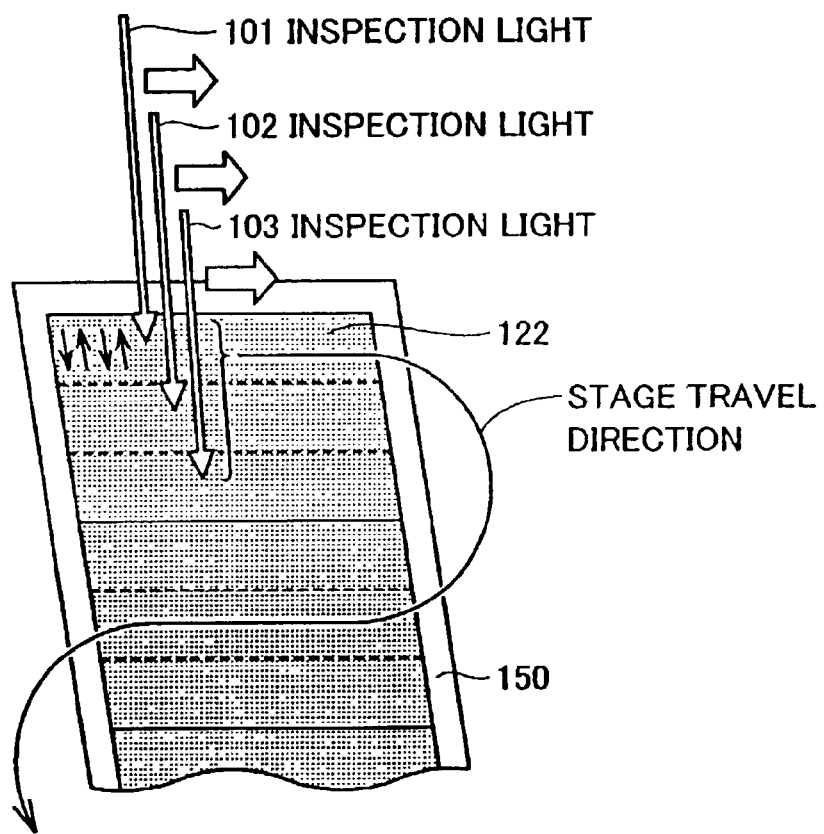
FIG. 11 is an illustration related to a general pattern inspection method.
Figure 12:
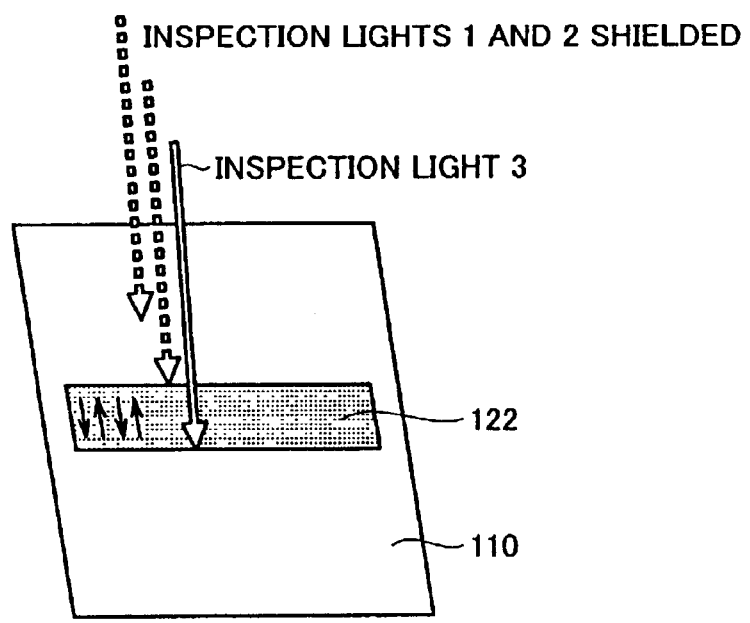
FIG. 12 is an illustration related to a conventional sensitivity adjusting method for pattern inspection apparatus.

In FIG. 9, the programmed defects in the reference pattern are intrusion defects 25a, 25b and 25c on the edges of shielding films. FIG. 10 is a variation of the reference patterns according to an eighth embodiment of the present invention. In FIG. 10, the base pattern is a hole pattern 13. With such a transparent programmed defects also, the detection limitation with respect to the size of the defects can be checked, hence the defect detection sensitivity can be checked quantitatively.

(Ninth Embodiment)

A sensitivity adjusting substrate in the sensitivity adjusting method according to a ninth embodiment of the present invention is characterized in that the programmed defects in the reference patterns are made to have higher transparency by reducing the thickness of the light shielding films. By employing the reference pattern having programmed defects of increased transparency, the detection sensitivity for defects or foreign object associated with extraordinary transparency can be checked and respective optical systems associated with inspection lights can be adjusted.

(Tenth Embodiment)

A sensitivity adjusting substrate in the sensitivity adjusting method according to a tenth embodiment of the present invention is characterized in that the reference patterns have a plurality of similar base patterns and programmed defects arranged at angles of 0°, 90° or other angle with respect to the scanning direction of the inspection lights. By employing patterns arranged in such angles, detection characteristics for defects specific to the scanning direction of the inspection lights can easily be checked.

(Eleventh Embodiment)

A sensitivity adjusting substrate in the sensitivity adjusting method according to an eleventh embodiment of the present invention is characterized in that a reference mark is arranged inside or outside of the reference pattern regions which is to be a point of origin of the defects to be detected. By the arrangement of above reference mark, the coordinates of the defects can be associated to the size of the defects or the like. Thus, detection sensitivity can be quantitatively and efficiently checked.

(Twelfth Embodiment)

The sensitivity adjusting substrate in the sensitivity adjusting method according to a twelfth embodiment of the present invention is characterized in that the light shielding film is altered to be transmissive, and is a halftone phase shift mask in which the phases of light transmissive film portion and quartz portion are inverted. By employing such halftone phase shift mask, the resolution of the patterns on the wafer can be improved. Specifically, a semi-transparent defects can be formed which are difficult to be detected when using the substrate structure formed with a normal light shielding film portion and the quartz portion. Accordingly, sensitivity check of an inspection apparatus of higher sensitivity can be performed efficiently.

(Thirteenth Embodiment)

The sensitivity adjusting substrate in the sensitivity adjusting method according to a thirteenth embodiment of the present invention is characterized in that a semiconductor wafer or a liquid crystal panel is used. By using the semiconductor wafer or the liquid crystal panel as the sensitivity adjusting substrate, these devices can be subjected to the inspection to find defects of the pattern formed thereon rather easily.

(Fourteenth Embodiment)

The sensitivity adjusting substrate in the sensitivity adjusting method according to a fourteenth embodiment of the present invention is characterized in that a silicon substrate on which a resist is patterned or a silicon substrate of which $SiO_2$ film on the surface is etched and thus patterned is used for the semiconductor wafer as a sensitivity adjusting substrate. By using the reference patterns in which the $SiO_2$ film is etched, aging of the surface of the sensitivity adjusting substrate is suppressed, and thus the substrate will be applicable to use for checking detection sensitivity over a long period.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A sensitivity adjusting method for a pattern inspection apparatus, inspecting a pattern formed during manufacture of a device with a plurality of inspection lights, comprising the steps of:

preparing sensitivity adjusting substrate divided into a plurality of regions to which identical reference patterns are respectively provided; and scanning said reference patterns with said plurality of inspection lights making one of said plurality of inspection lights respectively correspond to one of said reference patterns, after attaching said sensitivity adjusting substrate to said pattern inspection apparatus.

2. The sensitivity adjusting method for a pattern inspection apparatus according to claim 1, wherein said one of reference pattern includes a base pattern configured with a combination of a line pattern and a space pattern, and a programmed defect which is a defective portion having at least one of light transmittance, refractive index or thickness different from those of said base pattern.

3. The sensitivity adjusting method for a pattern inspection apparatus according to claim 2, wherein said one of reference pattern is configured with a simulation pattern region in which programmed defects are arranged in said base pattern, and defect-free pattern region configured with the base pattern.

4. The sensitivity adjusting method for a pattern inspection apparatus according to claim 3, wherein said programmed defects are regularly arranged in order of size.

5. The sensitivity adjusting method for a pattern inspection apparatus according to claim 3, wherein said programmed defects are arranged at predetermined angle with respect to the scanning direction of said inspection lights in said reference pattern.

6. The sensitivity adjusting method for a pattern inspection apparatus according to claim 1, wherein in the step of scanning with said plurality of lights, said sensitivity adjusting substrate is scanned with said plurality of lights using at least one of a travel of stage to which said sensitivity adjusting substrate is mounted, and a travel of said inspection lights employing a deflection element for deflecting said inspection lights.

7. The sensitivity adjusting method for a pattern inspection apparatus according to claim 1, wherein either one of a laser light and a mercury lamp is employed as a source of said plurality of inspection lights.

8. The sensitivity adjusting method for a pattern inspection apparatus according to claim 1, wherein at least one of an imaging element and a photomultiplier tube is applied to a photodetector unit for receiving inspection lights being directed to said reference pattern and transmitted through or reflected on said reference pattern.

9. The sensitivity adjusting method for a pattern inspection apparatus according to claim 1, wherein said sensitivity adjusting substrate is either one of a semiconductor substrate and a liquid crystal panel substrate.

10. The sensitivity adjusting method for a pattern inspection apparatus according to claim 9, wherein said sensitivity adjusting substrate is either one of a silicon substrate on which a resist is patterned and a silicon substrate of which $SiO_2$ film on the surface is patterned.

* * * * *